United States Patent [19]
Kopetzki

[11] Patent Number: 6,136,564
[45] Date of Patent: Oct. 24, 2000

[54] PROCESS FOR THE PRODUCTION OF PEPTIDES BY WAY OF STREPTAVIDIN FUSION PROTEINS

[75] Inventor: Erhard Kopetzki, Penzberg, Germany

[73] Assignee: Roche Diagnostics GmbH, Mannheim, Germany

[21] Appl. No.: 09/068,738

[22] PCT Filed: Nov. 6, 1996

[86] PCT No.: PCT/EP96/04850

§ 371 Date: Jun. 25, 1998

§ 102(e) Date: Jun. 25, 1998

[87] PCT Pub. No.: WO97/18314

PCT Pub. Date: May 22, 1997

[30] Foreign Application Priority Data

Nov. 16, 1995 [DE] Germany .................. 195 42 702

[51] Int. Cl.[7] .............. C12N 15/09; C12N 1/20; C97H 21/04; A61K 38/24; C07K 14/00
[52] U.S. Cl. ............ 435/69.4; 536/23.4; 530/399; 530/402; 435/320.1; 435/252.3; 435/254.2
[58] Field of Search .............. 435/69.4, 320.1, 435/252.3; 530/402, 399; 438/254.2; 536/23.4

[56] References Cited

FOREIGN PATENT DOCUMENTS

| 0 528 686 | 2/1993 | European Pat. Off. |
|---|---|---|
| 2 180 539 | 4/1987 | United Kingdom . |
| 88/06596 | 9/1988 | WIPO . |
| 86/02077 | 4/1989 | WIPO . |
| 89/03422 | 4/1989 | WIPO . |
| 91/06564 | 5/1991 | WIPO . |

OTHER PUBLICATIONS

Saito et al. Journal of Biochemistry, vol. 102, No. 1, Jul. 1987, pp. 111–122, "Bacterial synthesis of recombinant alpha human atrial natriuretic polypeptide".

Gardella et al. Journal of Biochemistry, vol. 265, No. 26, Sep. 15, 1990, pp. 15854–15859, "Expression of human parathyroid hormain–(1–84) in *Escherichia coli* as a Factor X–cleavable fusion protein".

Wingender et al., Journal of Biochemistry, vol. 264, No. 8, Mar. 15, 1989, pp. 4367–4373, "Expression of human parathyroid hormone in *Escherichia coli*".

*Primary Examiner*—Karen Cochrane Carson
*Assistant Examiner*—Devesh Srivastava
*Attorney, Agent, or Firm*—Arent Fox Kintner Plotkin Kahn

[57] ABSTRACT

The invention relates to a process for recombinant preparation of peptides by expression of a DNA in micro-organisms, which DNA codes for a fusion protein made of streptavidin and one of the said peptides. Streptavidin and the peptide are bound by a peptide sequence which can be cleaved by an endoproteinase. The process also includes isolation of the insoluble, inactive protein, solublisation of the inactive protein using a denaturant, dilution of the denaturant at a pH value of between 8.5 and 11 until cleaving of the fusion protein by an endoproteinase can take place, cleaving of the fusion protein, lowering of the pH value until streptavin and non-cleaved fusion protein precipitate, and cleaning of the desired peptide from the supernatant. Said process is particularly suitably for producing parathromone and urodilatin and fragments thereof.

13 Claims, 3 Drawing Sheets

A

```
EcoRI  NheI                                                           NotI
5'-AATTCGCTAGCGTTGACGACGATGACAAAACGGCGCCGCGTTCCCTGCGTAGATCTTCCTGCTTCGGC    -3'
3'-     GCGATCGCAACTGCTGCTACTGTTTTGCCGCGGCGCAAGGGACGCATCTAGAAGGACGAAGCCGCCGG-5'
        AlaSerValAspAspAspAspLysThrAlaProArgSerLeuArgArgSerSerCysPheGlyGly
    --- Core-SA||Enteroki.-Linker||-----  Urodilatin(95-126)  --------------->
```

B

```
NotI                                                              HindIII
5'-GGCCGCATGGACCGTATCGGTGCTCAGTCCGGACTGGGTTGCAACTCCTTCCGTTACTAATGA    -3'
3'-    CGTACCTGGCATAGCCACGAGTCAGGCCTGACCCAACGTTGAGGAAGGCAATGATTACTTCGA-5'
       ArgMetAspArgIleGlyAlaGlnSerGlyLeuGlyCysAsnSerPheArgTyrStop
                ------  Urodilatin(95-126)   ------|
```

```
     EcoRI    NheI                                                                                    NotI
5'-AATTCGCTAGCGTTGACGACGATGACAAAACGGGCGCCCGCGTTCCCTGCGTAGATCTTCCTGCTTCGGC  -3'
3'-    GCGATCGCAACTGCTGCTACTGTTTGCCCGCGGGCGCAAGGGACGCATCTAGAAGGACGAAGCCGCCGG-5'
           AlaSerValAspAspAspAspLysThrAlaProArgSerLeuArgArgSerCysPheGlyGly
       --- Core-SA||Enteroki.-Linker||-----  Urodilatin(95-126)   ---------->
```

B

```
   NotI                                                                                    HindIII
5'-GGCCGCATGGACCGTATCGGTGCTCAGTCCGACTGGGTTGCAACTCCTTCCGTTACTAATGA     -3'
3'-    CGTACCTGGCATAGCCACGAGTCAGGCCTGACCCAACGTTGAGGAAGGCAATGATTACTTCGA-5'
       ArgMetAspArgIleGlyAlaGlnSerGlyLeuGlyCysAsnSerPheArgTyrStop
       -----  Urodilatin(95-126)   -----|
```

```
        EcoRI  NheI                                                              NcoI
5'-aattcGCTAGCGGTACCGTCGACGACGATGACAAATCCGTTTCCGAAATCCAGCTGATGCACAACCTGGGTAAACACCTGAACTC   -3'
3'-    gCGATCGCCATGGCAGCTGCTGCTACTGTTTAGGCAAAGGCTTTAGGTCGACTACTGTGTTGGACCCATTTGTGGACTTGAGGTAC-5'
           AlaSerGlyThrValAspAspAspLysSerValSerGluIleGlnLeuMetHisAsnLeuGlyLysHisLeuAsnSerMet
       --- Core-SA|| Enterokinaselinker  ||----  PTH(1-37)  ---------------------------->
```

D

```
        NcoI                                                                    HindIII
5'-CATGGAACGTGTTGAATGGCTGCGTAAAAAAACTGCAGGACGTTCACAACTTCGTTGCTCTGTAATGA           -3'
3'-    CTTGCACAACTTACCGACGCATTTTTTTGACGTCCTGCAAGTGTTGAAGCAACGAGACATTACTTCGA-5'
           GluArgValGluTrpLeuArgLysLysLysLeuGlnAspValHisAsnPheValAlaLeuStop
       -----------------------  PTH(1-37)  -----------------|
```

```
     NheI                                                                          (PvuII)
5'-CTAGCCCGGGGTGACTTCCTGGCTGAAGGTCTGGTTCCGCGTTCCGTTCCGAAATCCAGCTG-3'
3'-    GGGCCCACTGAAGGACCGACTTCCAGACCAAGGCGCAAGGCAAGGCTTTAGGTCGAC-5'
       SerProGlyAspPheLeuAlaGluGlyLeuValProArgSerValSerGluIleGlnLeu
core-SA||------ Thrombin-Linker ------||---  PTH(1-37)   --->
```

F

```
     NheI                                                                          (PvuII)
5'-CTAGCGGATCCGAAAACCTGTACTTCCAGTCCGTTTCCGAAATCCAGCTG-3'
3'-    GCCTAGGCTTTTGGACATGAAGGTCAGGCAAAGGCTTTAGGTCGAC-3'
       AlaSerGlySerGluAsnLeuTyrPheGlnSerValSerGluIleGlnLeu
core-SA||--- TEV NIa-Linker ---||---  PTH(1-37)   --->
```

PROCESS FOR THE PRODUCTION OF PEPTIDES BY WAY OF STREPTAVIDIN FUSION PROTEINS

The invention concerns a process for the recombinant production of peptides by expression of fusion proteins with streptavidin and subsequent enzymatic cleavage of the fusion protein.

Peptides are usually understood as substances which are composed of up to ca. 100 amino acids. Such peptides can either be prepared chemically (Kent, S. B. H. et al. (1988) (1), Hodson, J. H., (1993) (2) or recombinantly (Kopetzki, E. et al. (1994) (3) Winnacker, E. -L. (1987) (4), Harris, T. J. R. (1983) (5)).

The disadvantages of chemical peptide synthesis are in particular that an economic synthesis is only possible up to ca. 30 to 40 amino acids and undesired modifications (false sequences, non-cleaved protective groups) are frequently formed during the synthesis. Further problems are racemization during fragment coupling, difficulties in cleaving the protective groups and finally the complicated purification.

Various methods can be used for the recombinant production of peptides. For example a direct expression can take place in the cytoplasm of microorganisms or cell lines. However, a minimum polypeptide length of ca. 80–100 amino acids is required for this. Smaller peptides are not stable and are degraded by proteolysis. Moreover these proteins usually contain an additional N-terminal methionine and the yields are very low.

The production of such peptides can be improved by the expression of soluble fusion proteins with a selective cleavage sequence and subsequent release of the desired peptide by chemical or enzymatic cleavage (Itakura, K. et al. (1977) (20); EP-B 0 001 930 (21); Gram, H. et al. (1994) (19); Sharma, A. et al., (1992) (22)). However, a particular disadvantage of soluble fusion proteins is that they can already be degraded by proteolysis in the cell or during secretion and processing mainly in the non-structured peptide region.

The production of streptavidin fusion proteins is described in EP-B 0 198 015, by Sano, T. (1991) (9) and Sano, T. (1992) (10). Such chimeric proteins in the case of Sano comprise the amino acids 16–133 of streptavidin as the streptavidin moiety, a polylinker and the sequence of the target protein. The target proteins described by Sano are the mouse metallothionein I protein and the T7 gene 10 protein. However, these chimeric proteins contained no cleavage site by means of which the target protein can be cleaved again from the streptavidin moiety. The production of streptavidin fusion proteins in Streptomyces is described in EP-B 0 198 015. However, the isolation of the peptide component from the fusion protein is very complicated. Thus for example an affinity chromatography using iminobiotin as the ligand must be carried out both before and after the cleavage.

The object of the present invention was to provide a process by which peptides can be produced via streptavidin fusion proteins in a high yield and purity with separation from the streptavidin component that is as complete as possible.

The object is achieved according to the invention by a process for the recombinant production of a peptide by expression of a DNA in microorganisms, preferably prokaryotes, which codes for a fusion protein comprising streptavidin and the said peptide wherein streptavidin and the peptide are linked via a peptide sequence which can be cleaved by an endoproteinase, isolation of the insoluble inactive fusion protein, solubilization of the inactive protein with a denaturing agent, dilution of the denaturing agent at a pH value between 8.5 and 11 until it is possible to cleave the fusion protein by an endoproteinase, cleavage of the fusion protein, lowering the pH value until the cleaved streptavidin and non-cleaved fusion protein precipitate and purification of the desired peptide from the supernatant.

The process according to the invention utilizes the advantage that streptavidin fusion proteins can be expressed very well in prokaryotes and can be isolated in the form of insoluble inactive proteins (inclusion bodies). Streptavidin fusion proteins solubilized in denaturing agents can be diluted at pH values above 8.5 to the extent that they can be digested with an endoproteinase without precipitating.

A further important advantage of the process according to the invention is that a renaturation of the fusion protein to form the active protein is not necessary. Finally the released streptavidin and optionally non-cleaved streptavidin fusion protein can be separated from the desired peptide by precipitation at pH values below 6. The process according to the invention is suitable for the production of numerous short-chain peptides. The process is particularly suitable for the production of natriuretic peptides and parathyroid hormone peptides.

Natriuretic peptides (NP peptides) are peptides with a natriuretic activity which are formed from a precursor polypeptide (prohormone) in the ventricle of the heart, the adrenal gland and the brain and have a ring of 17 amino acids as a structural element which is formed by a disulfide bridge between two cysteine residues. Precursor polypeptides are for example the "atrial" natriuretic peptide (ANP 1–126) or cardiodilatin (CCD 1–126) and the "brain" natriuretic peptides of the B and C type. Preferred NP peptides are derived from human α atrial natriuretic peptide (hαANP). In this case the C-terminal hαANP fragments of amino acids 95–126, 99–126 and 102–126 are particularly preferred.

Urodilatin (CDD 95–126) is a natriuretic peptide which can be isolated from human urine (Forssmann, K. et al., (1988) (23)). The peptide has a length of 32 amino acids, forms a ring of 17 amino acids by the formation of a disulfide bridge between two cysteine residues and is a member of the cardiodilatin/"atrial" natriuretic peptide (CDD/ANP) family. Like α-ANP (99–126) it is formed from the ANP propeptide (ANP 1–126). Urodilatin (CCD 95–126) is presumably formed in vivo by cleavage of this propeptide between the amino acids 94 and 95. The ca. 3.5 kDa urodilatin peptide differs from the α-ANP (99–126) peptide by a 4 amino acid extension at the N-terminus. The amino acid sequence and the structure of urodilatin are described for example in Drummer, C. et al., (1993) (24). Urodilatin binds to the membranous ANP receptors A and B and activates an intracellular guanylate cyclase coupled to the receptor. This causes the formation of the second messenger cGMP which mediates the diuretic and natriuretic effects in the kidney and the relaxing effect on the smooth vascular muscles (Heim, J. M., (1989) (25)). Consequently urodilatin is a preferred therapeutic for the prophylaxis and therapy of acute renal failure e.g. in patients after heart or liver transplantations (Bub, A. et al., (1992) (26); Drummer, C. et al., (1991) (27) and (1992) (28); Emmeluth, C. et al., (1992) (29); Goetz, K. L. et al., (1990) (30)).

The process according to the invention can also be used advantageously to produce parathyroid hormone (PTH) as well as fragments thereof. The DNA and amino acid sequence of PTH is described for example in Rokkones, E. et al. (1994) (16). The human parathyroid hormone gene codes for a pre-pro-PTH protein of 115 amino acids. After cleavage of the signal sequence and the prosegment the mature PTH hormone has 84 amino acids (PTH 1–84). It has been shown that PTH that is recombinantly produced in *E. coli* and *S. cerevisiae* is unstable and is rapidly degraded. The production of PTH fusion proteins is described by Forsberg, G. et al. (1991) (17). For this a nucleic acid is prepared which codes for a fusion protein composed of mature PTH (1–84) and a 15 kD IgG binding protein. A cleavage site for thrombin or subtilisin is inserted between both protein components. This fusion protein is also unstable and is already degraded to a considerable extent during expression in *E. coli*. It was also not possible to prevent degradation of PTH (1–84) by secretion of the mature PTH (1–84) hormone into the periplasm of *E. coli* using the protein A signal sequence. The half-life of PTH (1–84) in *E. coli* is only a few minutes.

The production of PTH (1–84) in *E. coli* via a fusion protein that can be cleaved with factor Xa is described by Gardella, T. J. et al (1990) (18). However, cleavage by factor Xa is very incomplete (ca. 50% cleavage after two hours) or also leads to the degradation of PTH (1–84) after a longer incubation with factor Xa.

The production of a PTH fragment (PTH 1–38) in *E. coli* by means of a fusion protein is also described by Gram, H. et al. (1994) (19). An Asp-Pro-Pro linker is used for the cleavage of the C-terminally fused PTH (1–38) peptide. This can be cleaved/removed by means of a 2-step process. In a first reaction the acid-labile Asp-Pro-peptide bond is chemically hydrolysed (incubation of the fusion protein in 60 mM HCl for 24 hours at 50° C.). Afterwards the remaining N-terminal Pro-Pro-dipeptide is enzymatically removed in a second reaction using dipeptidyl peptidase IV from *L. lactis*. However, this process is very time-consuming and a large amount of by-products is formed by the acid hydrolysis.

The fusion proteins can be cleaved enzymatically with a specifically cleaving proteinase (restriction proteinase). The proteinase is selected taking into consideration the amino acid sequence of the peptide to be produced. Care must be taken that, if possible, the recognition/cleavage sequence of the restriction proteinase does not occur in the desired peptide and preferably also not in the carrier component (streptavidin component) of the fusion protein i.e. it should only occur once in the cleavage region (linker region). Suitable specifically cleaving endoproteinases are for example enterokinase, factor Xa, thrombin, subtilisin BPN variants/ubiquitin protein peptidase, renin, collagenase, trypsin, chymotrypsin, endoproteinase Lys-C, kallikrein (Carter, P., (12)), TEV proteinase (Parks, T. D. et al., Anal. Biochem. 216 (1994) 413–417) (36), IgA proteinase (Pohlner, J. et al., Nature 325 (1987) 458–462) (37), Kex2p proteinase (EP-A 0 467 839) (38) or *S. aureus* V8 proteinase.

Endoproteinase LysC is preferably used which specifically cleaves proteins and peptides at the C-terminal end of lysine. Such an enzyme is for example known from fungi or bacteria (DE 30 34 045 C2). Endoproteinase LysC is particularly suitable for producing peptides that do not contain a lysine residue such as urodilatin.

A peptide sequence which can be cleaved by an endoproteinase is understood within the sense of the present invention as a short-chain peptide sequence which is preferably composed of 5–15 amino acids and contains a C-terminal cleavage site for the desired endoproteinase. This linker preferably additionally contains a combination of several amino acids at the N-terminal side at the desired endoproteinase recognition sequence selected from the amino acids Gly, Thr, Ser, Ala, Pro, Asp, Glu, Arg and Lys. A linker is particularly preferably used in which 2–8 of these additional amino acids are the negatively charged amino acids Asp and/or Glu.

A DNA coding for the fusion protein can be produced by known processes as described in Sambrook, J. et al. (1989) (6).

Streptavidin as described in EP-B 0 198 015 (7) and EP-A 0 612 325 (8) can for example be used as streptavidin. Further streptavidin derivatives or streptavidin fragments as described for example by Sano, T. et al., (9) are also suitable. A streptavidin is preferably used which is truncated (shortened) at the N-terminus and/or C-terminus. This prevents aggregation and proteolysis (Sano, T. et al., (9)). A streptavidin is preferably used which begins with the amino acids 10–20 and ends with the amino acids 130–140 (numbering analogous to Argarana C. E. et al.(1986) (33)). A streptavidin composed of the amino acids 16–133 or 13–139 is particularly preferably used.

The fusion proteins are produced by expression of a DNA (nucleic acid sequence) which codes for the fusion protein in microorganisms and preferably in prokaryotes. The expression vector used should not contain any elements that would mediate secretion of the protein into the medium so that the protein can be formed in a denatured, insoluble form (inclusion bodies). A DNA that is suitable for the expression can preferably be produced by synthesis. Such processes are familiar to a person skilled in the art and are described for example in Beattie K. L. and Fowler, R. F. (1991) (34); EP-B 0 424 990 (35); Itakura, K. et al., (1977) (20). It may also be expedient to modify the nucleic acid sequence of the proteins according to the invention. Such modifications are for example:

Modification of the nucleic acid sequence in order to introduce various recognition sequences of restriction enzymes to facilitate the steps of ligation, cloning and mutagenesis.

Modification of the nucleic acid sequence to incorporate preferred codons for the host cell.

Extension of the nucleic acid sequence with additional regulation and transcription elements in order to optimize the expression in the host cell.

All further steps in the process for the production of suitable expression vectors and for the expression are state of the art and familiar to a person skilled in the art. Such methods are described for example in Sambrook, J. et al. (1989) (6).

Fusion proteins can accumulate in prokaryotes as well as in other cells such as in eukaryotic host cells such as yeasts (e.g. saccharomyces, pichia, hansenula and kluyveromyces) and fungi such as aspergillus and trichoderma in the form of insoluble protein aggregates, so-called inclusion bodies (IBs). Inclusion bodies are formed when the rate of synthesis of the protein in the cell is larger than the rate of folding to the active native protein. In this case the protein aggregates in the cell preferably in the cytoplasm. Here the protein is stored in the cell in a denatured, compressed and insoluble form. This reduces interference of cell function to a minimum.

Escherichia, Streptomyces or Bacillus are for example suitable as prokaryotic host organisms. For the production of the fusioh proteins according to the invention the microorganisms, preferably prokaryotes, are transformed in the usual manner with the vector which contains the DNA coding for the fusion protein and subsequently fermented in the usual manner. After lysis of the cells the insoluble inactive protein (IBs) is isolated in the usual manner for example by centrifugation (pellet fraction). The desired insoluble protein aggregates can if necessary be further enriched by washing the pellets e.g. with buffers containing detergents.

The IBs are solubilized by processes familiar to a person skilled in the art with a denaturing agent such as guanidine hydrochloride, urea or urea derivative (cf. e.g. U.S. Pat. No. 5,453,363) and transferred to a suitable non-denaturing buffer (pH>8.5) by dilution or dialysis. In this process the dilution is carried out in such a manner that the remaining denaturing agent does not have a significant effect on the enzymatic hydrolysis of the fusion protein.

The dilution is preferably carried out in a pulse-like manner for example by adding the IB solubilisate dropwise to the buffer (pH>8.5) that contains no denaturing agent.

Such a pulse-like dilution enables an almost simultaneous removal of the effect of the denaturing agent and separation of the molecules to be solubilized. This largely avoids an undesired intermolecular interaction (aggregation) of the molecules to be solubilized.

Surprisingly it has turned out that fusion proteins produced by the process according to the invention are not degraded in the host cells and can be completely cleaved enzymatically without significant cleavage in the peptide component itself (e.g. PTH or urodilatin).

The process according to the invention is particularly suitable for the production of urodilatin, parathyroid hormone or fragments thereof. Urodilatin fragments of amino acids 95–126, 99–126 or 102–126 (See SEQ ID NO:17) as well as the parathyroid hormone fragment of amino acids 1–37 (See ID NO:16) are especially preferably produced.

The following examples, publications, the sequence protocols and the figures further elucidate the invention the protective scope of which derives from the patent claims. The described processes are to be understood as examples which still describe the subject matter of the invention even after modifications.

BRIEF DESCRIPTION OF THE DRAWINGS

FIG. 1 shows the DNA segments A and B obtained according to example 1.

FIG. 2 shows the DNA segments C and D obtained according to example 2.

FIG. 3 shows the DNA segment E obtained according to example 3 and the DNA segment F obtained according to example 4.

EXAMPLE 1

Construction of the core-SA-URO(95–126) fusion gene containing an endoproteinase linker (plasmid: pSA-EK-URO)

core-SA: shortened streptavidin of amino acids Met-(13–139) URO (95–126): urodilatin or cardiodilatin fragment of amino acids 95–126 (sequence described by Drummer, C. et al., (1993) (24)) (SEQ ID NO:17).

The expression vector for the core-SA-URO (95–126) fusion gene containing an endoproteinase LysC cleavage site is based on the expression vector pSAM-CORE for core streptavidin. The construction and description of the plasmid pSAM-CORE is described in WO 93/09144 (11). In order to construct core-SA fusion proteins the singular NheI restriction cleavage site located at the 3' end before the stop codon of the core-SA gene is used.

A ca. 140 bp long DNA fragment coding for the linker [VDDDDK] (SEQ ID NO:1) and the urodilatin (95–126) polypeptide [TAPRSLRRSSCFGGRMDRIGAQSGLGCNSFRY] (SEQ ID NO:2) was composed of 2 ca. 70 bp long chemically synthesized DNA segments. The codons preferably used in E. coli (E. coli codon usage) were taken into account in the gene design and the ends of the individual DNA segments were provided with suitable singular restriction endonuclease cleavage sites.

In two reaction mixtures the complementary oligonucleotides 1 (SEQ ID NO:3) and 2 (SEQ ID NO:4)
1 AATTCGCTAGCGTTGACGACGATGA-CAAAACGGCGCCGCGTTCCCTGCGTAGATCT TCCT-GCTTCGGC (SEQ ID NO:3)
2 GGCCGCCGAAGCAGGAAGATCTACG-CAGGGAACGCGGCGCCGTTTTGTCATCGTCG TCAACGCTAGCG (SEQ ID NO:4)
were annealed to the DNA segment A (FIG. 1) and the oligonucleotides 3 (SEQ ID NO:5) and 4 (SEQ ID NO:6)
3 GGCCGCATGGACCGTATCGGTGCT-CAGTCCGGACTGGGTTGCAACTCCTTCCGTTA CTAATGA (SEQ ID NO:5)
4 AGCTTCATTAGTAACGGAAGGAGTTG-CAACCCAGTCCGGACTGAGCACCGATACGG TCCATGC (SEQ ID NO:6)
were annealed to the DNA segment B (FIG. 1) (reaction buffer: 12.5 mmol/l Tris-HCl, pH 7.0 and 12.5 mmol/l MgCl$_2$; oligonucleotide concentration: in each case 1 pmol/60 µl) and the hybridization products A and B were each subcloned into the polylinker region of the E. coli pUCBM21 vector (Boehringer Mannheim GmbH, Mannheim, Germany) (DNA segment A, cleavage sites: EcoRI and NotI; DNA segment B, cleavage sites: NotI and HindIII). The DNA sequence of the two subcloned DNA segments was confirmed by DNA sequencing. Afterwards the expression plasmid pSA-EK-URO for the core-SA-URO (95–126) fusion gene was assembled in a three fragment ligation from the Nhe/NotI DNA segment A, the NotI/HindIII DNA segment B and the ca. 2.9 kBp long NheI/HindIII-pSAM-CORE vector fragment. In this process the DNA segments A and B were isolated by double digestion with the appropriate endonucleases from the corresponding pUCBM21 plasmid derivatives. The desired plasmid pSA-EK-URO was identified by restriction mapping and the DNA sequence of the linker urodilatin region was again checked by DNA sequencing.

EXAMPLE 2

Construction of the core-SA-PTH(1–37) fusion gene containing an enterokinase linker (plasmid: pSA-EK-PTH)

PTH(1–37): parathyroid hormone fragment of amino acids 1–37, amino acid sequence described by Handy, G. N. et al., Proc. Natl. Acad. Sci. USA 78 (1981) 7365–7369 (39) (SEQ ID NO:16).

The vector pSA-EK-PTH for the expression of the core-SA-PTH(1–37) fusion gene containing an enterokinase cleavage site was prepared according to the strategy described in example 1 for the core-SA-URO(95–126). fusion gene containing an enterokinase cleavage site.

In two reaction mixtures the complementary oligonucleotides 5 (SEQ ID NO:7) and 6 (SEQ ID NO:8)
5 AATTCGCTAGCGGTACCGTCGACGAC-GATGACAAATCCGTTTCCGAAATCCAGCT GATGCA-CAACCTGGGTAAACACCTGAACTC (SEQ ID NO:7)
6 CATGGAGTTCAGGTGTTTACCCAGGT-TGTGCATCAGCTGGATTTCGGAAACGGAT TTGT-CATCGTCGTCGACGGTACCGCTAGCG (SEQ ID NO:8)
were annealed to the DNA segment C (FIG. 2) and the oligonucleotides 7 (SEQ ID NO:9) and 8 (SEQ ID NO:10)
7 CATGGAACGTGTTGAATGGCTGCG-TAAAAAACTGCAGGACGTTCACAACTTCGTT GCTCTGTAATGA (SEQ ID NO:9)
8 AGCTTCATTACAGAGCAACGAAGTTGT-GAACGTCCTGCAGTTTTTTACGCAGCCA TTCAA-CACGTTC (SEQ ID NO:10)

were annealed to the DNA segment D (FIG. 2) (reaction buffer: 12.5 mmol/l Tris-HCl, pH 7.0 and 12.5 mmol/l MgCl$_2$; oligonucleotide concentration: in each case 1 nmol/60 µl) and the hybridization products C and D were each subcloned into the polylinker region of the E. coli pUCBM21 vector (DNA segment C, cleavage sites: EcoRI and NcoI; DNA segment D, cleavage sites: NcoI and HindIII). The DNA sequence of the two subcloned DNA segments was confirmed by DNA sequencing. Afterwards the expression plasmid pSA-EK-PTH for the core-SA-EK-PTH(1–37) fusion gene was assembled in a three fragment ligation from the NheI/NcoI DNA segment C, the NcoI/HindIII DNA segment D and the ca. 2.9 kBp long NheI/HindIII-pSAM-CORE vector fragment. In this process the DNA segments C and D were isolated from the corresponding pUCBM21 plasmid derivatives by double digestion with the appropriate endonucleases. The desired plasmid pSA-EK-PTH was identified by restriction mapping and the DNA sequence of the enterokinase linker PTH region was again checked by DNA sequencing.

EXAMPLE 3

Construction of the core-SA-PTH(1–37) fusion gene containing a thrombin linker (plasmid: pSA-THRO-PTH)

The plasmid pSA-THRO-PTH is derived from the core-SA-EK-PTH expression plasmid pSA-EK-PTH (see example 2) by replacing the coding region for the enterokinase linker by a thrombin linker.

The amino acid sequence of the thrombin linker used [GDFLAEGLVPR] (SEQ ID NO:15) is based on the natural thrombin cleavage site in fibrinogen (amino acid position: 6–16) and the minimum recognition sequence for thrombin (Carter, P. in: Ladisch, M. R.; Willson, R. C.; Painton, C. C.; Builder, S. E. eds. (1990) (12)).

For this the plasmid pSA-EK-PTH was digested with NheI and PvuII, the ca. 2.9 kBp long NheI/PvuII-pSA-EK-PTH vector fragment was isolated and ligated to the DNA segment E (FIG. 3) prepared by hybridization of the 2 complementary oligonucleotides 9 (SEQ ID NO:11) and 10 (SEQ ID NO:12).
9 CTAGCCCGGGTGACTTCCTGGCTGAAG-GTCTGGTTCCGCGTTCCGTTTCCGAAATC CAG (SEQ ID NO:11)
10 CTGGATTTCGGAAACGGAACGCGGAAC-CAGACCTTCAGCCAGGAAGTCACCCGG G (SEQ ID NO:12)

The desired plasmid construction pSA-THRO-PTH was identified by restriction mapping and the replaced linker region was checked by DNA sequencing.

EXAMPLE 4

Construction of the core-SA-PTH(1–37) fusion gene containing a TEV linker (plasmid: pSA-TEV-PTH)

The plasmid pSA-TEV-PTH is derived from the core-SA-EK-PTH expression plasmid pSA-EK-PTH (see example 2) by replacing the coding region for the enterokinase linker by a TEV linker.

The plant virus TEV NIa proteinase ("tobacco etch virus") recognises the amino acid sequence ENLYFQ↓G/S and cleaves between Gln and Gly or Ser (Dougherty, W. G. et al., (1988)) (13). The recombinantly produced enzyme was obtained from GIBCO BRL (Life Technologies, Inc. Gaithersburg, Md., USA).

For this the plasmid pSA-EK-PTH was digested with NheI and PvuII, the ca. 2.9 kBp long NheI/PvuII-pSA-EK-PTH vector fragment was isolated and ligated to the DNA segment F (FIG. 3) prepared by hybridization of the 2 complementary oligonucleotides 11 (SEQ ID NO:13) and 12 (SEQ ID NO:14).
11 CTAGCGGATCCGAAAACCTGTACTTC-CAGTCCGTTTCCGAAATCCAG (SEQ ID NO:13)
12 CTGGATTTCGGAAACGGACTGGAAGTA-CAGGTTTTCGGATCCG (SEQ ID NO:14)

The desired plasmid construction pSA-TEV-PTH was identified by restriction mapping and the replaced linker region was checked by DNA sequencing.

EXAMPLE 5

Expression of the core-SA fusion proteins in E. coli

For the expression of the core-SA fusion proteins the E. coli K12 strain RM82 (a methionine revertant of ED 8654, Murray, N. E. et al. (1977) (14)) was transformed with one of the expression plasmids pSA-EK-URO, pSA-EK-PTH, pSA-THRO-PTH and pSA-TEV-PTH (ampicillin resistance) described in examples 1–4 and with the lacI$^q$ repressor plasmid pUBS500 (kanamycin resistance, preparation and description see: EP-A 0368342).

The RM82/pUBS500/pSA-EK-URO, RM82/pUBS500/pSA-EK-PTH, RM82/pUBS500/pSA-THRO-PTH and RM82/pUBS500/pSA-TEV-PTH cells were cultured up to an optical density at 550 nm of 0.6–0.9 in DYT medium (1% (w/v) yeast extract, 1% (w/v) Bacto Tryptone (Difco, Detroit, USA) and 0.5% NaCl) containing 50 mg/l ampicillin and 50 mg/l kanamycin and subsequently induced with IPTG (isopropyl-β-D-thiogalactoside) (final concentration 1–5 mmol/l). After an induction phase of 4–8 hours, the cells were harvested by centrifugation and the cell pellets were washed with 25 mmol/l potassium phosphate buffer pH 7.5.

Expression Analysis

The cell pellets from in each case 1 ml centrifuged culture medium (RM82/pUBS500/pSA-EK-URO, RM82/pUBS500/pSA-EK-PTH, RM82/pUBS500/pSA-THRO-PTH and RM82/pUBS500/pSA-TEV-PTH cells) were resuspended in 0.25 ml 10 mmol/l phosphate buffer, pH 6.8 and 1 mmol/l EDTA and the cells were lysed by ultrasonic treatment.

After centrifugation ⅕ volume 5×SDS sample buffer (1×SDS sample buffer: 50 mmol/l Tris-HCl, pH 6.8, 1% SDS, 1% mercaptoethanol, 10% glycerol, 0.001% bromophenol blue) was added to the supernatant. The insoluble cell debris fraction was resuspended in 0.3 ml 1×SDS sample buffer containing 6–8 M urea, the samples were incubated for 5 minutes at 95° C. and centrifuged. Afterwards the proteins were separated by SDS polyacrylamide gel electrophoresis (PAGE) (Laemmli, U. K. (1970) (15)) and stained with Coomassie brilliant blue R dye.

The core-SA fusion proteins synthesized in E. coli were homogeneous and were found exclusively in the insoluble cell debris fraction (IBs). The expression yield for the core-SA fusion proteins was 30–50% relative to the total E. coli protein.

EXAMPLE 6

Cell lysis and preparation of inclusion bodies (IBs)

200 g (wet weight) E. coli RM82/pUBS500/pSA-EK-URO, RM82/pUBS500/pSA-EK-PTH, RM82/pUBS500/pSA-THRO-PTH and RM82/pUBS500/pSA-TEV-PTH cells was suspended in 1 l 0.1 mol/l Tris-HCl, pH 7.0 at 0° C., 300 mg lysozyme was added and incubated for 20 minutes at 0° C. Afterwards the cells were completely lysed mechanically by means of high pressure dispersion and the DNA was digested within 30 minutes at 25° C. by adding 2 ml 1 mol/l MgCl$_2$ and 10 mg DNAse (Boehringer Mannheim # 154709). Subsequently 500 ml 60 mmol/l EDTA, 6% Triton® X100 and 1.5 mol/l NaCl, pH 7.0 was added to the lysis solution and incubated for a further 30 minutes at 0° C. Afterwards the insoluble components (cell debris and IBs) were sedimented by centrifugation.

The pellet was suspended in 1 l 0.1 mol/l Tris-HCl, 20 mmol/l EDTA pH 6.5, incubated for 30 minutes at 25° C. and the IB preparation was isolated by centrifugation.

Solubilization of the IBs 25 g IB pellet (wet weight) was suspended by stirring for 2 hours at 25° C. in 200 ml 10 mmol/l Tris-HCl buffer, 8 mol/l urea, 10 mmol/l EDTA pH 7.0. The insoluble components were separated by centrifugation and the clear supernatant was processed further.

EXAMPLE 7
Dilution of the solubilisate

The dilution was carried out in a BioFlo II fermenter (New Brunswick Scientific Co., Inc. Edison, N.J., USA) at 25° C. while stirring (300 rpm) by continuous addition of 200 ml core-SA fusion protein solubilisate to 3.8 l 50 mmol/l Tris HCl pH 9.0 using a pump (output: 15–40 ml/h).

EXAMPLE 8
Enzymatic cleavage of the core-SA fusion proteins
Enterokinase Cleavage (ValAsp4Lys cleavage sequence)

The core SA fusion proteins having an enterokinase cleavage site were digested in 50 mmol/l Tris-HCl, pH 8.0 at 30° C. at a concentration of 0.3 to 3 mg/ml and a substrate/proteinase ratio of 1:20 to 1:250 (enterokinase, restriction proteinase from calf intestine, Boehringer Mannheim, Mannheim, Germany) and the time course of the enzymatic cleavage (kinetics) was analysed by analytical reversed phase HPLC (see example 9.1). For this purpose samples (10 to 100 μl) were removed from the reaction mixture at intervals of 1 to 3 hours over a period of 6 to 24 hours.

LysC Endoproteinase Cleavage (Lys cleavage site)

The core-SA-EK-URO fusion protein was digested in 50 mmol/l Tris-HCl, pH 8.0 at 30 to 35° C. at a concentration of 0.3 to 3 mg/ml and a substrate/proteinase ratio of 1:1000 to 1:25,000 (LysC endoproteinase from Lysobacter enzymogenes, sequencing grade; Boehringer Mannheim, Mannheim, Germany) and the time course of the enzymatic cleavage was analysed by analytical reversed phase HPLC (see example 9.1). For this purpose samples (10 to 100 μl) were removed from the reaction mixture at intervals of 1 to 3 hours over a period of 6 to 24 hours.

Thrombin cleavage (GDFLAEGLVPR cleavage sequence)

The core-SA-THRO-PTH fusion protein was digested in 50 mmol/l Tris-HCl, pH 8.8 at 25 to 30° C. at a concentration of 0.3 to 3 mg/ml and a substrate/proteinase ratio of 1:50 to 1:500 (thrombin from human plasma, Boehringer Mannheim, Mannheim, Germany) and the time course of the enzymatic cleavage was analysed by analytical reversed phase HPLC (see example 9.1). For this purpose samples (10 to 100 μl) were removed from the reaction mixture at intervals of 1 to 3 hours over a period of 6 to 24 hours.

TEV NIa proteinase cleavage (GluAsnLeuTyrPheGln↓Gly/Ser cleavage sequence)

The core-SA-TEV-PTH fusion protein was digested in 50 mmol/l Tris-HCl, pH 8.0, 0.5 mmol/l EDTA and 1 mmol/l DTT at 30° C. at a concentration of 0.3 to 3 mg/ml and a substrate/ proteinase ratio of 1:50 to 1:500 (recombinant TEV NIa restriction proteinase, GIBCO BRL Life Technologies, Inc. Gaithersburg, Md., USA) and the time course of the enzymatic cleavage was analysed by analytical reversed phase HPLC (see example 9.1). For this purpose samples (10 to 100 μl) were removed from the reaction mixture at intervals of 1 to 3 hours over a period of 6 to 24 hours.

EXAMPLE 9
Separation of core-8A and non-cleaved core-SA fusion protein by precipitation The released core-SA carrier protein and non-cleaved core-SA fusion protein were precipitated from the cleavage preparation by lowering the pH (pH<6). The cleavage mixture was admixed with 1 mol/l citric acid to a final concentration of 25 mmol/l and adjusted to pH 3.0 and the precipitate was separated by centrifugation or filtration.

EXAMPLE 10
Purification of the peptides URO (95–126) and PTH (1–37)

The enzymatically released peptides can be further purified with chromatographic methods that are known to a person skilled in the art.

10.1 Purification of the peptides by cation exchange chromatography on Fractogel EMD-SO$_3$ 650(M)

The cleavage mixture was loaded onto a Fractogel EMD-SO$_3$—650(M) column (3×40 cm, V=283 ml) from the Merck Company (Darmstadt, Germany) equilibrated with 25 mmol/l citric acid, pH 3.0 (1 CV/h) and washed with the equilibration buffer until the absorbance of the eluate at 280 nm reached the blank value of the buffer. The bound material was eluted by a gradient of 0 to 1 mmol/l NaCl in equilibration buffer (10 to 20 CV, 1 CV/h).

10.2 Purification of the peptides by reversed phase HPLC

After pre-purification of the peptides by means of cation exchange chromatography (see: example 10.1), an aliquot of 1 to 2 ml (ca. 100 to 300 μg) was further purified by semipreparative RP-HPLC with fractionation.

Chromatography conditions:

Column: Eurospher 100-C$_8$, 5 μm (4×250 mm, V=3.17 ml) (Knauer, Berlin, Germany)

Sample volume: 1–2 ml (100–300 μg protein)

Detector: UV, 220 nm

Flow rate: 0.5 ml/min

Mobile solvent:
  A: 0.13% TFA in H$_2$O
  B: 0.1% TFA, 80% acetonitrile, 20% H$_2$O (v/v)

EXAMPLE 11
Analytical reversed phase (HPLC)

The analytical reversed phase (HPLC) was carried out with a Europher column (Europher 100-C$_8$, 5 μm (4×250 mm, V=3.17 ml, Knauer, Berlin, Germany). The sample volume was 10–100 μl corresponding to 1–100 μg protein. The detection was carried out with a UV detector at 220 nm. It was chromatographed at a flow rate of 0.5 ml/min.

Mobile solvent:
  A: 0.13% trifluoroacetic acid in H$_2$O (gradient 100-0% in 50 min)
  B: 0.1% trifluoroacetic acid, 80% acetonitrile, 20% H$_2$O (v/v) (gradient 0–100% in 50 min).

EXAMPLE 12
Characterization of the purified peptides

The identity and purity of the purified peptides was examined in comparison to a chemically synthesized standard by mass spectroscopy (PD-MS and laser desorption spectroscopy), analytical reversed phase HPLC, isoelectric focussing (Bark, J. E. et al., J. Forensic Sci. Soc. 16 (1976) 115–120 (42), SDS PAGE (Laemmli, U. K., Nature 227 (1970) 680–685 (43)) and capillary electrophoresis.

List of references

1) Kent, S. B. H. et al., Banburi Rep. 29 (1988) 3–20
2) Hodson, J. H., Bio/Technology 11 (1993) 1309–1310

3) Kopetzki, E. et al., Clin. Chem. 40 (1994) 688–704
4) Winnacker, E. -L., (1987) VCH Publishers, Weinheim and New York (1987)
5) Harris, T. J. R. In: Genetic Engineering (Williamson, R. ed.), Academic Press, London, vol. 4 (1983) 127–185
6) Sambrook, J. et al. (1989) In: Molecular cloning: A laboratory manual. Cold Spring Harbor Laboratory Press, Cold Spring Harbor, N.Y.
7) EP-B 0 198 015
8) EP-A 0 612 325
9) Sano, T. Biochem. Biophys. Res. Commun. 176 (1991) 571–577
10) Sano, T. et al., Proc. Natl. Acad. Sci., USA 89 (1992) 1534–1538
11) WO 93/09144
12) Carter, P. In: Ladisch, M. R.; Willson, R. C.; Painton, C. C.; Builder, S. E. eds. Protein Purification: From Molecular Mechanisms to Large-Scale Processes. ACS Symposium Series No. 427, American Chemical Society, (1990) 181–193
13) Dougherty, W. G. et al., EMBO J. 7, (1988) 1281–1287
14) Murray, N. E. et al., Mol. Gen. Genet. 150 (1977) 53–61
15) Laemmli, U. K., Nature 227 (1970) 680–685
16) Rokkones, E. et al., J. Biotechnol. 33 (1994) 293–306
17) Forsberg, G. et al., J. Prot. Chem. 10 (1991) 517–526
18) Gardella, T. J. et al., J. Biol. Chem. 265 (1990)
19) Gram, H. et al., Bio/Technology 12 (1994) 1017–1023
20) Itakura, K. et-al., Science 198 (1977) 1056–1063
21) EP-B 0 001 930
22) Sharma, A. et al., Proc. Natl. Acad. Sci. USA 89 (1992) 1534–1538
23) Forssmann, K. et al., Clin. Wochensch. 66 (1988) 752–759
24) Drummer, C. et al., Pflügers Archiv., European J. of Physiol. 423 (1993) 372–377
25) Heim, J. M., Biochem. Biophys. Res. Commun. 163 (1989) 37–41
26) Bub, A. et al., Histochem. J. (Suppl.) 24 (1992) 517
27) Drummer, C. et al., J. Am. Soc. Nephrol. 1 (1991) 1109–1113
28) Drummer, C. et al., Am. J. Physiol. 262 (1992) F 744–754
29) Emmeluth, C. et al., Am. J. Physiol. 262 (1992) F 513–F 516
30) Goetz, K. L. et al., J. Am. Soc. Nephrol. 1 (1990) 867–874
31) DE 30 34 045 C2
32) Allen, G. et al., J. Cell. Sci. Suppl. 3 (1985) 29
33) Argarana C. E. et al., Nucl. Acids. Res. 14 (1986) 1871–1882
34) Beattie, K. L. and Fowler, R. F., Nature 352 (1991) 548–549
35) EP-B 0 424 990
36) Parks, T.D. et al., Anal. Biochem. 216 (1994) 413–417
37) Pohlner, J. et al., Nature 325 (1987) 458–462
38) EP-A 0 467 839
39) Handy, G. N. et al., Proc. Natl. Acad. Sci., USA 78 (1981) 7365–7369

What is claimed is:

1. A process for recombinantly producing a peptide, the process comprising
   expressing, in a microorganism, a DNA which codes for a fusion protein comprising a streptavidin and the peptide to be produced, wherein the streptavidin and the peptide are linked via a cleavage sequence which is cleavable by a factor Xa or thrombin endoproteinase, to produce an insoluble fusion protein;
   isolating the insoluble fusion protein;
   solubilizing the fusion protein in a solution comprising a denaturing agent and adjusting the solution to a pH value of between 8.5 and 11;
   cleaving the fusion protein via the cleavage sequence using a factor X or thrombin endoproteinase to produce streptavidin cleavage segments and peptide cleavage segments;
   precipitating the streptavidin cleavage segments and uncleaved fusion protein from the solution by lowering the pH value of the solution; and
   purifying the peptide from the solution supernatant.

2. The process of claim 1, wherein the microorganism is prokaryotic.

3. The process of claim 2, wherein the insoluble fusion protein is isolated in inactive form.

4. The process of claim 3, wherein the insoluble fusion protein is isolated in an inclusion body.

5. The process of claim 1, wherein, in said precipitating step, the pH value of the solution is lowered below 6.

6. The process of claim 1, wherein the peptide to be produced is a natriuretic peptide or a parathyroid hormone peptide.

7. The process of claim 1, wherein the peptide to be produced is a urodilatin peptide or a parathyroid hormone peptide.

8. The process of claim 7, wherein the peptide to be produced is selected from the group consisting of a urodilatin peptide of amino acids 95–126 (SEO ID NO:2), a urodilatin peptide of amino acids 99–126 (amino acids 5–32 of SEQ ID NO:2), a urodilatin peptide of amino acids 102–126 (amino acids 8–32 of SEO ID NO:2) and a parathyroid hormone peptide of amino acids 1–37 (SEO ID NO:16).

9. The process of claim 1, wherein the cleavage sequence contains 5–15 amino acids and a C-terminal cleavage site.

10. The process of claim 9, wherein the cleavage sequence further contains a linker sequence comprising a plurality of amino acids attached at the N-terminal of the cleavage sequence, wherein each amino acid of the plurality of amino acids is independently selected from the group consisting of Gly, Thr, Ser, Ala, Pro, Asp, Glu, Arg and Lys.

11. The process of claim 10, wherein the linker sequence comprises 2–8 amino acids each of which is independently selected from the group consisting of Asp and Glu.

12. The process of claim 1, wherein the microorganism is eukaryotic.

13. The process of claim 1, wherein the solution is brought to a pH value of between 8,5 and 11 using art aqueous buffer.

* * * * *

UNITED STATES PATENT AND TRADEMARK OFFICE
CERTIFICATE OF CORRECTION

PATENT NO.  : 6,136,564
DATED       : October 24, 2000
INVENTOR(S) : Kopetzki

It is certified that error appears in the above-identified patent and that said Letters Patent is hereby corrected as shown below:

Title page,

Item [54], please delete --PROCESS FOR THE PRODUCTION OF PEPTIDES BY WAY OF STREPTAVIDIN FUSION PROTEINS--, and insert-- PROCESS FOR THE PREPARATION OF PEPTIDES BY WAY OF STREPTAVIDIN FUSION PROTEINS.

Signed and Sealed this

Fifteenth Day of May, 2001

*Attest:*

NICHOLAS P. GODICI

*Attesting Officer*      *Acting Director of the United States Patent and Trademark Office*

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 1:

Val Asp Asp Asp Asp Lys
1               5

(2) INFORMATION FOR SEQ ID NO: 2:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 2:

Thr Ala Pro Arg Ser Leu Arg Arg Ser Ser Cys Phe Gly Gly Arg Met
1               5                   10                  15

Asp Arg Ile Gly Ala Gln Ser Gly Leu Gly Cys Asn Ser Phe Arg Tyr
                20                  25                  30

(2) INFORMATION FOR SEQ ID NO: 3:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic
            oligonucleotide"

(xi) SEQUENCE DESCRIPTION: SEQ ID NO: 3:

```
AATTCGCTAG CGTTGACGAC GATGACAAAA CGGCGCCGCG TTCCCTGCGT AGATCTTCCT     60

GCTTCGGC                                                              68
```

(2) INFORMATION FOR SEQ ID NO: 4:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic
            oligonucleotide"

(xi) SEQUENCE DESCRIPTION: SEQ ID NO: 4:

```
GGCCGCCGAA GCAGGAAGAT CTACGCAGGG AACGCGGCGC CGTTTTGTCA TCGTCGTCAA     60

CGCTAGCG                                                              68
```

(2) INFORMATION FOR SEQ ID NO: 5:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic
            oligonucleotide"

(xi) SEQUENCE DESCRIPTION: SEQ ID NO: 5:

```
GGCCGCATGG ACCGTATCGG TGCTCAGTCC GGACTGGGTT GCAACTCCTT CCGTTACTAA     60

TGA                                                                   63
```

(2) INFORMATION FOR SEQ ID NO: 6:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic
            oligonucleotide"

(xi) SEQUENCE DESCRIPTION: SEQ ID NO: 6:

```
AGCTTCATTA GTAACGGAAG GAGTTGCAAC CCAGTCCGGA CTGAGCACCG ATACGGTCCA     60

TGC                                                                   63
```

(2) INFORMATION FOR SEQ ID NO: 7:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "synthetic
             oligonucleotide"

(xi) SEQUENCE DESCRIPTION: SEQ ID NO: 7:

AATTCGCTAG CGGTACCGTC GACGACGATG ACAAATCCGT TTCCGAAATC CAGCTGATGC      60

ACAACCTGGG TAAACACCTG AACTC                                            85

(2) INFORMATION FOR SEQ ID NO: 8:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "synthetic
             oligonucleotide"

(xi) SEQUENCE DESCRIPTION: SEQ ID NO: 8:

CATGGAGTTC AGGTGTTTAC CCAGGTTGTG CATCAGCTGG ATTTCGGAAA CGGATTTGTC      60

ATCGTCGTCG ACGGTACCGC TAGCG                                            85

(2) INFORMATION FOR SEQ ID NO: 9:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "synthetic
             oligonucleotide"

(xi) SEQUENCE DESCRIPTION: SEQ ID NO: 9:

CATGGAACGT GTTGAATGGC TGCGTAAAAA ACTGCAGGAC GTTCACAACT TCGTTGCTCT      60

GTAATGA                                                                67

(2) INFORMATION FOR SEQ ID NO: 10:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: other nucleic acid
        (A) DESCRIPTION:  /desc = "synthetic
             oligonucleotide"

(xi) SEQUENCE DESCRIPTION: SEQ ID NO: 10:

AGCTTCATTA CAGAGCAACG AAGTTGTGAA CGTCCTGCCG TTTTTTACGC AGCCATTCAA      60

CACGTTC                                                                67

(2) INFORMATION FOR SEQ ID NO: 11:

(i) SEQUENCE CHARACTERISTICS:
        (A) LENGTH: 59 base pairs
        (B) TYPE: nucleic acid -continued (C) STRANDEDNESS: single
      (D) TOPOLOGY: linear (ii) MOLECULE TYPE: other nucleic acid
      (A) DESCRIPTION: /desc = "synthetic
          oligonucleotide"

(xi) SEQUENCE DESCRIPTION: SEQ ID NO: 11:

CTAGCCCGGG TGACTTCCTG GCTGAAGGTC TGGTTCCGCG TTCCGTTTCC GAAATCCAG      59

(2) INFORMATION FOR SEQ ID NO: 12:

(i) SEQUENCE CHARACTERISTICS:
      (A) LENGTH: 55 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic
          oligonucleotide"

(xi) SEQUENCE DESCRIPTION: SEQ ID NO: 12:

CTGGATTTCG GAAACGGAAC GCGGAACCAG ACCTTCAGCC AGGAAGTCAC CCGGG      55

(2) INFORMATION FOR SEQ ID NO: 13:

(i) SEQUENCE CHARACTERISTICS:
      (A) LENGTH: 47 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic
          oligonucleotide"

(xi) SEQUENCE DESCRIPTION: SEQ ID NO: 13:

CTAGCGGATC CGAAAACCTG TACTTCCAGT CCGTTTCCGA AATCCAG      47

(2) INFORMATION FOR SEQ ID NO: 14:

(i) SEQUENCE CHARACTERISTICS:
      (A) LENGTH: 43 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "synthetic
          oligonucleotide"

(xi) SEQUENCE DESCRIPTION: SEQ ID NO: 14:

CTGGATTTCG GAAACGGACT GGAAGTACAG GTTTTCGGAT CCG      43

(2) INFORMATION FOR SEQ ID NO: 15:

(i) SEQUENCE CHARACTERISTICS:
      (A) LENGTH: 11 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 15:

Gly Asp Phe Leu Ala Glu Gly Leu Val Pro Arg
1               5                   10

```
-continued (2) INFORMATION FOR SEQ ID NO: 16:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 16:

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
            20                  25                  30

Asn Phe Val Ala Leu
        35

(2) INFORMATION FOR SEQ ID NO: 17:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 17:

Thr Ala Pro Arg Ser Leu Arg Arg Ser Ser Cys Phe Gly Gly Arg Met
 1               5                  10                  15

Asp Arg Ile Gly Ala Gln Ser Gly Leu Gly Cys Asn Ser Phe Arg Tyr
            20                  25                  30
```